United States Patent [19]
Milcent et al.

[11] Patent Number: 5,100,910
[45] Date of Patent: Mar. 31, 1992

[54] ARYL SUBSTITUTED TETRAZOLE DERIVATIVES, AND APPLICATION THEREOF IN THERAPEUTICS

[75] Inventors: René L. Milcent, Paris; Luc Lebreton, Maisons Laffitte; Fathi Mazouz, Antony; Claude Burstein, Coye La Foret; Salah Gueddari, Noisy Le Grand, all of France

[73] Assignee: Delalande S.A., Courbevoie, France

[21] Appl. No.: 357,421

[22] Filed: May 25, 1989

[30] Foreign Application Priority Data

May 27, 1988 [FR] France .................. 88 07114

[51] Int. Cl.$^5$ ............... C07D 207/04; A61K 31/41
[52] U.S. Cl. .................... 514/381; 548/252
[58] Field of Search ................ 548/252; 514/381

[56] References Cited

U.S. PATENT DOCUMENTS

| | | |
|---|---|---|
| 3,453,285 | 7/1969 | Hayao et al. ............ 548/252 |
| 3,509,153 | 2/1970 | Hayao et al. ............ 548/252 |
| 3,865,570 | 2/1975 | George et al. ........... 71/92 |

FOREIGN PATENT DOCUMENTS

| | | |
|---|---|---|
| 0028305 | 5/1981 | European Pat. Off. . |
| 1084633 | 1/1955 | France . |
| 1163355 | 9/1969 | United Kingdom . |

*Primary Examiner*—David B. Springer
*Attorney, Agent, or Firm*—Flynn, Thiel, Boutell & Tanis

[57] ABSTRACT

Compounds for therapeutic use of formula:

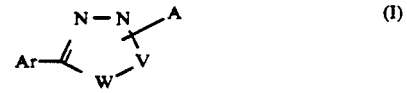

where the chain —W—V—N— represents —N=N—N—, —N—N=N—, —O—CO—N—, —O—CS—N—, —S—CO—N— or —S—CS—N—; Ar is an aryl group; and A is a vinyl group or an alkylene chain terminated by CN, methoxy, ethoxy, OH, halogen or NH$_2$ which may possibly be substituted.

19 Claims, No Drawings

ARYL SUBSTITUTED TETRAZOLE DERIVATIVES, AND APPLICATION THEREOF IN THERAPEUTICS

The present invention relates to new (hetero)aryl substituted diazole derivatives, the method of preparing them and application thereof in therapeutics.

The derivatives of the invention correspond more precisely to the formula:

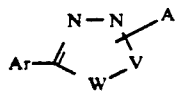

in which the chain

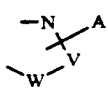

represents 1) either the chain of structure:

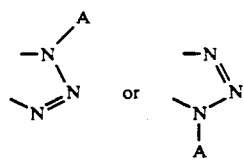

where A is:
a) a vinyl group or a $(CH_2)_n$—$Z_1$ group in which $Z_1$ represents a CN, methoxy or ethoxy group and n is an integer from 1 to 6, in which case Ar takes on the value $Ar_1$ which represents:
a phenyl nucleus,
a phenyl nucleus substituted by one or two halogen atoms or an $NO_2$, methyl, ethyl, methoxy, ethoxy, phenyl or benzyloxy group of formula:

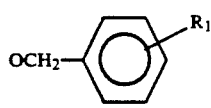

where $R_1$ represents a hydrogen atom, one or two halogen atoms or a CN, $NO_2$, $NH_2$, $CF_3$, $C_1$–$C_4$ alkyl, $C_1$–$C_4$ alkoxy or $C_2$–$C_4$ acylamino group, or
a heterocyclic nucleus; or
b) a group of formula $(CH_2)_m$—$Z_2$ in which $Z_2$ represents an OH group, a halogen atom, an $NH_2$ group, an $NH_2$ group substituted by one or two $C_1$–$C_4$ alkyl groups, a $C_2$–$C_4$ acylamino group or a phthalimido group and m is an integer from 2 to 6, in which case Ar takes on the value $Ar_2$ which represents:
a phenyl nucleus substituted by a $C_1$–$C_4$ alkoxy group or a benzyloxy group of formula

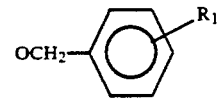

where $R_1$ has the same meaning as above, or a heterocyclic nucleus;
2) or the chain of structure

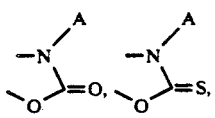

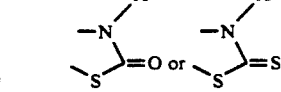

where A is a 2-cyano ethyl group, in which case Ar takes on the value $Ar_3$ which represents a phenyl nucleus substituted by a $C_1$–$C_4$ alkyl, $C_1$–$C_4$ alkoxy, phenyl or benzyloxy group of formula

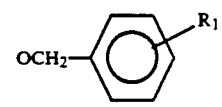

where $R_1$ has the same meaning as above,
as well as the acid addition salts of these derivatives (I) having a salifiable groupe,
to the exclusion of 5-phenyl 2-tetrazole butyronitrile and 5-phenyl 2-tetrazole valeronitrile.

It should be noted that in the foregoing and hereafter the expression "$C_1$–$C_4$ alkyl" relates to the methyl, ethyl, n-propyl, isopropyl, n-butyl, isobutyl, sec-butyl and tert-butyl groups; the expression "$C_1$–$C_4$ alkoxy" is equivalent to the expression "O-$C_1$–$C_4$ alkyl"; the expression "$C_2$–$C_4$ acylamino" comprises in particular the acetylamino and propionylamino groups; the term "halogen" relates to chlorine, bromine, iodine and fluorine; and the expression "heterocyclic nucleus" comprises particularly the pyridyl nucleus.

Among the derivatives of formula (I) those which are preferred have the following particular structures:

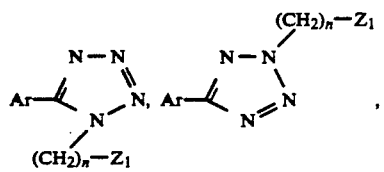

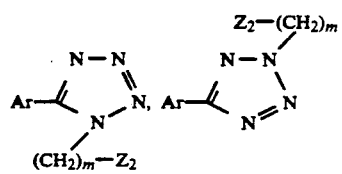

where $Z_1$=CN, n=1 or 2, $Z_2$=OH, m=integer from 2 to 6 Ar represents a phenyl nucleus para substituted by a benzyloxy group whose phenyl nucleus is possibly substituted by one or two halogen atoms, one $C_1$-$C_4$ alkyl group or one $C_1$-$C_4$ alkoxy group, and

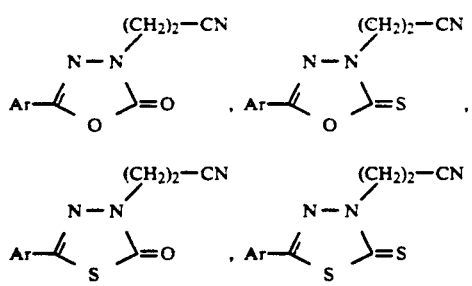

where Ar is a phenyl group para substituted by a benzyloxy group.

The present invention further extends to the method of preparing the derivatives of formula (I).

This method comprises more precisely:

(a) the condensation of the compounds of formula $$X\text{---}(CH_2)_n\text{---}Z_1 \qquad (IIa)$$

where n=integer from 1 to 6, $Z_1$=CN, methoxy or ethoxy and X represents a good leaving group such as a halogen atom or a mesyloxy or tosyloxy group, respectively with the compounds of formula

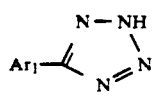     (IIIa)

where $Ar_1$ has the same meaning as in formula (I), in the presence of a strong base, particularly a mineral base such as KOH of NaOH, and in a solvent more particularly an alcohol solvent such as propanol, or else such as a metal hydride for example sodium hydride, and in an aprotic solvent such as DMF, which leads to the compounds of formula

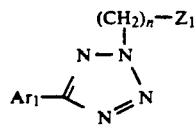     (Ia)

or

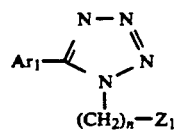     (Ib)

where $Ar_1$ has the same meaning as in formula (I) and $(CH_2)_n$—$Z_1$ has the same meaning as in the above formula (IIa);

(b) the condensation in the same conditions as in item (a) above of the compounds of formula $$X\text{---}(CH_2)_m\text{---}Z_{20} \qquad (IIb)$$

where m is an integer from 2 to 6, $Z_{20}$ represents OH, halogen, $NH_2$ substituted by two $C_1$-$C_4$ alkyl groups, $C_2$-$C_4$ acylamino or phthalimido and X has the same meaning as in formula (IIa), respectively with the compounds of formula

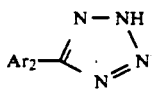     (IIIb)

where $Ar_2$ has the same meaning an in formula (I), which leads to the compounds of formula

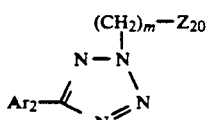     (Ic)

or

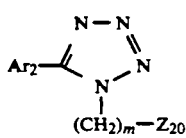     (Id)

where $Ar_2$ has the same meaning as in formula (I) and $(CH_2)_m$—$Z_{20}$ has the same meaning as in the above formula (IIb);

c) the action of $PCl_5$ then of hydrazoic acid, in an aprotic medium such as benzene, respectively on the compounds of formula $$Ar_1\text{---}CO\text{---}NH\text{---}(CH_2)_n\text{---}CN \qquad (IV)$$

where $Ar_1$ and n have the same meaning as in formula (I), particularly following the technique described by R. T. BUKLER in J. Med. Chem. 13, 725 (1970), which leads to the compounds of formula

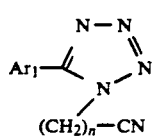     (I'b)

where $Ar_1$ and n have the same meaning as in formula (I);

d) the action of hydrazine or a hydrazine salt such as acetate or sulfate, particularly in an alcohol medium such as propanol, respectively on the compounds of formula

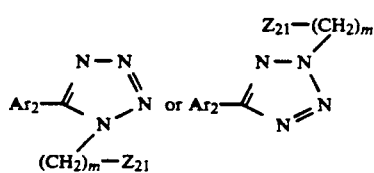

where m is an integer from 2 to 6 and $Z_{21}$ is an imido group such as phthalimido and $Ar_2$ has the same meaning as in formula (I), which leads to the compounds of formula

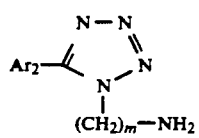     (Ie)

or

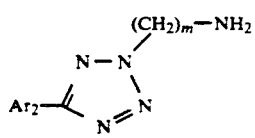
(If)

where m is an integer from 2 to 6 and $Ar_2$ has the same meaning as in formula (I);

e) the condensation, preferably in an aprotic solvent, on the compounds of formula (Ie) or (If) of a $C_1$-$C_4$ alkyl halide, particularly a $C_1$-$C_4$ alkyl iodide, which leads to the compounds of formula

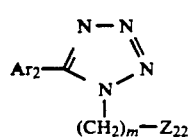
(Ig)

or

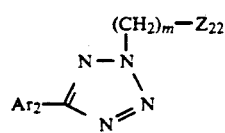
(Ih)

where m is an integer from 2 to 6 and $Z_{22}$=$NH_2$ substituted by a $C_1$-$C_4$alkyl group;

f) the action of a base such as ammonia for example, on the compounds of formula

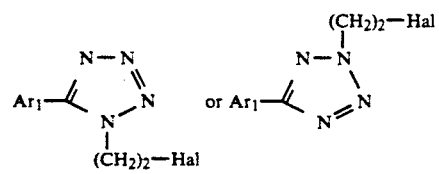

where Hal is a halogen atom, particularly a bromine atom and $Ar_1$ has the same meaning as in formula (I), which leads to the compounds of formula

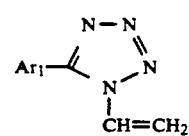
(Ii)

or

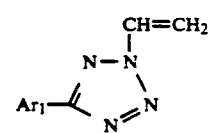
(Ij)

where $Ar_1$ has the same meaning as before; or g) the condensation of the compounds of formula

$Ar_3$—CT—NH—NH—$(CH_2)_2$—CN  (V)

where $Ar_3$ has the same meaning as in formula (I) and T is an oxygen or sulfur atom, which phosgene or thiophosgene, preferably in an aprotic medium such as dioxane, chloroform or toluene, which leads to the compounds of formula

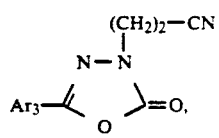
(Ik)

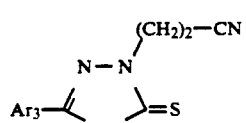
(Il)

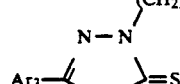

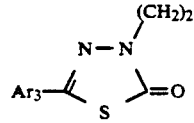
(Im)

or

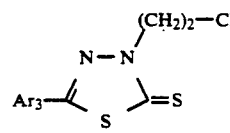
(In)

The compounds (IIIa) and (IIIb) may be prepared by the action of sodium azide on the compounds of formula

$Ar_1$—CN  (VIa)

or

$Ar_2$—CN  (VIb)

preferably in accordance with the technique described by R. H. Herbst in J. Org. Chem. 22, 1142 (1957).

The compounds (VIa) or (VIb) not known up to now, namely those for which $Ar_1$ or $Ar_2$ represents a phenyl nucleus substituted by a benzyloxy group whose phenyl nucleus has a substituent $R_1$, are obtained by treating the compound of formula

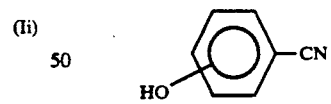
(VII)

by sodium hydride in an aprotic solvent such as DMF, then reacting the compound thus obtained respectively with the compounds of formula

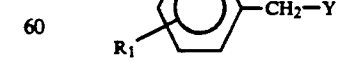
(VIII)

where Y is a good leaving group such as a halogen atom or a mesyloxy or tosyloxy group.

The compounds (V) for which T is an oxygen atom may be obtained either by action of (2-cyano ethyl) hydrazine on the methyl or ethyl esters of the acid of formula Ar₃—COOH in an alcohol medium, preferably ethanol, or by action of acrylonitrile in an alcohol medium, preferably 1-propanol, on the compounds of formula Ar₃—CO—NH—NH₂     (IX)

The compounds (V) for which T is a sulfur atom may be obtained by action of (2-cyano ethyl) hydrazine on the compounds of formula Ar₃—CS—S—CH₂—CO₂M     (X)

where M is an alkaline metal such as sodium or potassium.

The compounds (X) are obtained by action of a monohalogenoacetic acid such as monochloracetic acid, in an aqueous medium and in the presence of sodium or potassium carbonate, on the acids of formula Ar₃—CS—SH themselves obtained by the action of the magnesian Ar₃—Mg—Hal where Hal is a halogen atom on carbon sulfide in an aprotic and anhydrous medium such as THF.

The derivatives (I) having a salifiable group may be converted in salts by action of an organic or mineral acid, in an appropriate solvent.

The following preparations are given by way of examples for illustrating the invention.

EXAMPLE 1

5-[4-(3-chloro benzyloxy) phenyl] 2-tetrazole propanenitrile (Ia); Code number: 1

1st step: 4-(3-chloro benzyloxy) benzonitrile (VIa)

To a solution of 5×10⁻² mole of 4-hydroxy benzonitrile (VII) in 100 ml of DMF are added little by little 5×10⁻² mole of NaH so as to obtain a temperature of 25° C. Then the solution is heated to 50° C. until the release of hydrogen ceases. After cooling to 0° C., 5×10⁻² of 3-chloro benzyl chloride (VIII) is added little by little. The reaction mixture is heated to 40° C. for one hour then poured into 300 ml of iced water. The resultant solid is separated by filtration then recrystallized in an ethanol-water mixture, which leads to the expected compound.

Using this operating mode but from the appropriate starting products, the other compounds (VIa) are obtained and particularly those shown in table I hereafter.

2nd step: 5-[4-(3-chloro benzyloxy) phenyl] tetrazole (IIIa)

To a solution of 5×10⁻² mole of 4-(3-chloro benzyloxy) benzonitrile in 20 ml of butanol are added 6.6×10⁻² mole of sodium azide and 6.6×10⁻² of acetic acid. Then the reaction mixture is heated to reflux for four days. 1 g of sodium azide, 2 g of acetic acid and 10 ml of butanol are added and the medium is again heated for two days at reflux. After concentrating by evaporating the solvent, the residue is taken up in 20 ml of 10% aqueous NaOH. After filtration, the aqueous phase is extracted with ether. By acidification of the alkaline solution using HCl 2N, the expected compound precipitates and is recrystallized in methanol.

Using the same operating mode but from appropriate starting compounds, the other tetrazoles (IIIa) are obtained and particularly those shown in table II hereafter.

3rd step: 5-[4-(3-chloro benzyloxy) phenyl] 2-tetrazole propanenitrile (Ia)

To a solution made tepid of 10⁻² mole of 5-[4-(3-chloro benzyloxy) phenyl] tetrazole in 60 ml of n-propanol containing 10⁻² mole of KOH, 1.2×10⁻² mole of propionitrile bromide (IIa) is added and the reaction mixture is heated to reflux for 25 hours. After concentration by evaporating the solvent, the residue is taken up in ether, the etherated solution is washed twice with 20 ml of 0.5N aqueous NaOH, then with water, dried and concentrated. After recrystallization in methanol, the expected compound is obtained.

Using the same operating method but from appropriate reagents, the other compounds (Ia) are obtained and particularly those shown in table III hereafter.

EXAMPLE 2

5-[4-(4-methoxy benzyloxy) phenyl] 2-tetrazole ethanol [(Ic); code number: 42] and 5-[4-(4-methoxy benzyloxy) phenyl] 1-tetrazole ethanol [(Id); code number: 51]

To 30 ml of n-propanol are added 10⁻² mole of 5-[4-(4-methoxy benzyloxy) phenyl] tetrazole and 10⁻² mole of 2-bromo ethanol. The mixture is heated to reflux for 25 hours. The solvent is evaporated and the residue taken up in 100 ml of hot ether. The etherated solution is washed with 0.5N NaOH, then with water. After drying on sodium sulfate, the etherated phase is concentrated. The compound of code number 42 is obtained after recrystallization in methanol. The recrystallization solvent is concentrated and the residue is subjected to chromatography on a silica column (eluent:ethyl acetate/petroleum ether:¼) whereby the compound of code number 51 is isolated.

Using the same operating method but from appropriate reagents, the compounds (Ia), (Ib), (Ic), (Id) and (If) are obtained and particularly those shown in tables III to IV hereafter.

EXAMPLE 3

2-(2-dimethylamino ethyl) 5-(4-benzyloxy phenyl) tetrazole [(Oc); code number: 64]

To a solution of 2.52 g (10 mmoles) of 5-(4-benzyloxy phenyl) tetrazole in 40 ml of anhydrous DMF, are added 0.24 g (10 mmoles) of NaH. After release of hydrogen and heating in a water bath for 15 minutes, the temperature is lowered to 0° C. and a solution of 10 mmoles of 2-dimethylamino ethyl in 10 ml of DMF is added. The mixture is heated for 2 hours 30 mins in a water bath then cooled to room temperature and poured on iced water. The precipitate formed is filtered, dried and recrystallized.

Similarly, but from the appropriate reagents, the compounds of code numbers 65, 66 and 67 shown in table VI hereafter are obtained.

EXAMPLE 4

2-(2-amino ethyl) 5-(4-benzyloxy phenyl) tetrazole [(If); code number: 68]

A solution of 2 mmoles of the compound of code number 67 and 3 mmoles of hydrazine hydrate in 20 ml of 1-propanol is heated to reflux for 3 hours 30 mins. After cooling to 0° C., the phthahydrazide (F > 300° C.) is separated by filtration and washed with a little benzene. The filtrate is evaporated and the residue os recrystallized.

EXAMPLE 5

5-(4-benzyloxy phenyl) 2-vinyl tetrazole [(Ij); code number: 69]

To a suspension of 5 mmoles of the compound of code number 65 in 10 ml of aqueous ammonia, ethanol is added until a solution is obtained which is agitated for 2 hours at 25° C. The expected product is precipitated by addition of 100 ml of iced water. After filtration and drying, the product is recrystallized in petroleum ether with a quantitative yield.

melting point = 65° C.

IR ($\nu$ cm$^{-1}$): 1645, 1615.

NMR (DMSO d$_6$) $\delta$ ppm: 5.15 (s, 2H); 5.45 (d, 1H); 6.15 (d, 1H); 7.2 and 8.05 (2d, 4H); 7.3–7.9 (sm, 5H+1H).

TABLE I

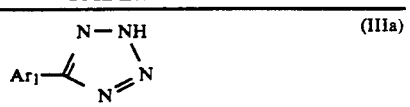

| Ar$_1$ | Yield (%) | Melting Point (°C.) |
|---|---|---|
| (Cl-2 $\phi$-CH$_2$O)-4 $\phi$- | 69 | 88 |
| (Cl-3 $\phi$-CH$_2$O)-4 $\phi$- | 76 | 91 |
| (diCl-2,4 $\phi$-CH$_2$O)-4 $\phi$- | 80 | 106 |
| (diCl-2,6 $\phi$-CH$_2$O)-4 $\phi$- | 77 | 132 |
| (CH$_3$-4 $\phi$-CH$_2$O)-4 $\phi$- | 60 | 111 |
| (CH$_3$-3 $\phi$-CH$_2$O)-4 $\phi$- | 55 | 105 |
| (CH$_3$-2 $\phi$-CH$_2$O)-4 $\phi$- | 90 | 81 |
| (CH$_3$O-4 $\phi$-CH$_2$O)-4 $\phi$- | 83 | 130 |
| (CH$_3$O-3 $\phi$-CH$_2$O)-4 $\phi$- | 61 | 98 |
| (F-4 $\phi$-CH$_2$O)-4 $\phi$- | 78 | 120 |
| (NO$_2$-4 $\phi$-CH$_2$O)-4 $\phi$- | 55 | 168 |
| (I-2 $\phi$-CH$_2$O)-4 $\phi$- | 77 | 90 |

TABLE II

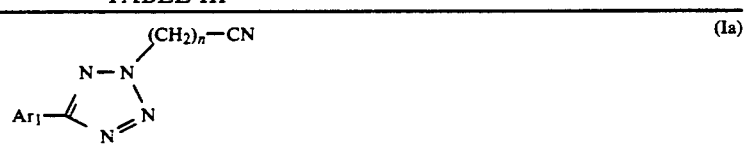

| Ar$_1$ | Yield (%) | Melting Point (°C.) |
|---|---|---|
| ($\phi$-CH$_2$O)-4 $\phi$- | 55 | 228 |
| (Cl-2 $\phi$-CH$_2$O)-4 $\phi$- | 52 | 188 |
| (Cl-3 $\phi$-CH$_2$O)-4 $\phi$- | 60 | 200 |
| (Cl-4 $\phi$-CH$_2$O)-4 $\phi$- | 61 | 240 |
| (diCl-2,4 $\phi$-CH$_2$O)-4 $\phi$- | 75 | 187 |
| (diCl-2,6 $\phi$-CH$_2$O)-4 $\phi$- | 67 | 224 |
| (diCl-3,4 $\phi$-CH$_2$O)-4 $\phi$- | 69 | 200 |
| $\phi$-4 $\phi$- | 72 | 242 |
| (CH$_3$-4 $\phi$-CH$_2$O)-4 $\phi$- | 78 | 240 |
| (CH$_3$-3 $\phi$-CH$_2$O)-4 $\phi$- | 37 | 184 |
| (CH$_3$-2 $\phi$-CH$_2$O)-4 $\phi$- | 43 | 190 |
| (CH$_3$O-4 $\phi$-CH$_2$O)-4 $\phi$- | 30 | 220 |
| (CH$_3$O-3 $\phi$-CH$_2$O)-4 $\phi$- | 50 | 228 |
| (F-4 $\phi$-CH$_2$O)-4 $\phi$- | 80 | 204 |
| (NO$_2$-4 $\phi$-CH$_2$O)-4 $\phi$- | 15 | 201 |
| (I-2 $\phi$-CH$_2$O)-4 $\phi$- | 46 | 207 |

TABLE III $$\text{Ar}_1 \overset{N-N}{\underset{N=N}{\bigtriangleup}} (CH_2)_n-CN \quad (Ia)$$

| Code No. | Ar$^1$ | n | Melting point (°C.) | Yield (%) | Recrystal. solvent | IR $\nu$ cm$^{-1}$ (KBr) | H$^1$ NMR $\delta$ p.p.m. (DMSO d$_6$) |
|---|---|---|---|---|---|---|---|
| 1 | (Cl-3 $\phi$-CH$_2$O)-4 $\phi$ | 2 | 93 | 41 | Me OH | 1600-10  N = 2240-2250 | 3.35(t, 2H), 5.05(t, 2H), 5.3(s, 2H) 7.1–8.2(m, 8H) |
| 2 | (pyridyl-4)- | 2 | 166 | 50 | Ac OEt | 1600-10  N = 2240-2250 | 3.3(t, 2H), 5.1(t, 2H), 8 et 8.85 (2d, 4H) |
| 3 | $\phi$- | 2 | 52 | 48 | Ac OEt/ petroleum ether | 1600-10  N = 2240-2250 | 3.3(t, 2H), 5(t, 24), 7.35–8.15 (m, 5H) |
| 4 | CH$_3$O-4 $\phi$- | 2 | 84 | 40 | Me OH | 1600-10  N = 2240-2250 | 3.3(t, 2H), 3.85(s, 3H)), 5.05(t, 2H) 7.15 et 8.1(2d, 4H) |
| 5 | NO$_2$-4 $\phi$- | 2 | 162 | 52 | Me OH | 1600-10  N = 2240-2250 | 3.35(t, 2H), 5.2(t, 2H), 8.4–8.6(m, 4H) |
| 6 | Cl-4 $\phi$- | 2 | 100 | 55 | Me OH | 1600-10  N = 2240-2250 | 3.3(t, 2H), 5.05(t, 2H), 7.65 et 8.1(2d, 4H) |
| 7 | ($\phi$-CH$_2$O)-4 $\phi$- | 2 | 128 | 61 | Me OH | 1600-10  N = 2240-2250 | 3.3(t, 2H), 5(t, 2H), 5.2(s, 2H), 7.15–8.2(m, 9H) |
| 8 | (Cl-2 $\phi$-CH$_2$O)-4 $\phi$ | 2 | 100 | 45 | Me OH | 1600-10  N = 2240-2250 | 3.2(t, 2H), 5.15(t, 2H), 5.25(s, 2H), 7.15–8.2(m, 8H) |
| 9 | (Cl-4 $\phi$-CH$_2$O)-4 $\phi$ | 2 | 154 | 46 | Me OH | 1600-10  N = 2240-2250 | 3.35(t, 2H), 5.1(t, 2H), 5.2(s, 2H), 7.15–8.2(m, 8H) |
| 10 | (di Cl-2,4 $\phi$-CH$_2$O)-4 $\phi$- | 2 | 144 | 52 | Me OH | 1600-10  N = 2240-2250 | 3.35(t, 2H), 5.05(t, 2H), 5.25(s, 2H), 7.2–8.25(m, 7H) |
| 11 | (di Cl-2,6 $\phi$-CH$_2$O)-4 $\phi$- | 2 | 124 | 60 | Me OH | 1600-10  N = 2240-2250 | 3.3(t, 2H), 5.05(t, 2H), 5.25(s, 2H), 7.2–8.25(m, 7H) |
| 12 | (di Cl-3,4 $\phi$-CH$_2$O)-4 $\phi$- | 2 | 136 | 57 | Me OH | 1600-10  N = 2240-2250 | 3.3(t, 2H), 5.05(t, 2H), 5.25(s, 2H), 7.15–8.2(m, 7H) |
| 13 | $\phi$-4 $\phi$- | 2 | 134 | 56 | Me OH | 1600-10  N = 2240-2250 | 3.3(t, 2H), 5(t, 2H), 7.25–8.15 (m, 9H) |
| 14 | $\phi$-4 $\phi$- | 3 | 86 | 38 | Me OH | 1600-10  N = 2240-2250 | 2.1–2.75(m, 4H), 4.8(t, 2H) 7.35–8.35(m, 9H) |
| 15 | $\phi$-4 $\phi$- | 4 | 132 | 43 | Me OH | 1600-10  N = 2240-2250 | 1.4–1.8(m, 2H), 1.85–2.25(m, 2H) 2.5(t, 2H), 4.8(t, 2H), 7.05–8.05(m, 9H) |
| 16 | $\phi$-4 $\phi$- | 6 | 100 | 40 | Me OH | 1600-10  N = 2240-2250 | 1.1–1.75(m, 6H), 1.8–2.15(m, 2H) 2.4(t, 2H), 4.7(t, 2H), 7.3–8.3 (m, 9H) |
| 29 | ($\phi$-CH$_2$O)-4 $\phi$- | 1 | 148 | 45 | AcOEt/ | 1615 | 5.2(s, 2H); 6.25(s, 2H); 7.1–7.5 |

TABLE III-continued (Ia)

$$Ar_1 \underset{N=N}{\overset{N-N-(CH_2)_n-CN}{\diagdown\diagup}}$$

| Code No. | Ar¹ | n | Melting point (°C.) | Yield (%) | Recrystal. solvent | IR ν cm⁻¹ (KBr) | H¹ NMR δ p.p.m. (DMSO d₆) |
|---|---|---|---|---|---|---|---|
| 31 | (CH₃-4 φ-CH₂O)-4 φ- | 1 | 152 | 33 | methanol | 1610 | (m, 7H); 8(d, 2H) 2.3(s, 3H); 5.15(s, 2H); 6.3 (s, 2H); 7.15-7.5(m, 6H); 8.05(d, 2H) |
| 32 | (CH₃-4 φ-CH₂O)-4 φ- | 2 | 140 | 40 | methanol | 2255, 1610 | 2.3(s, 3H); 3.3(t, 2H); 5.05 (t, 2H); 5.15(s, 2H); 7.1-7.5 (m, 6H) |
| 35 | (CH₃-3 φ-CH₂O)-4 φ- | 2 | 106 | 46 | methanol | 2250 | 2.3(s, 3H); 3.3(t, 2H); 5 (t, 2H); 5.15(s, 2H); 7.05-7.45 (m, 6H) |
| 37 | (CH₃-2 φ-CH₂O)-4 φ- | 1 | 134 | 50 | methanol | 1605 | 2.3(s, 3H); 5.15(s, 2H); 6.25 (s, 2H); 7.05-7.5(m, 6H); 8(d, 2H) |
| 38 | (CH₃-2 φ-CH₂O)-4 φ- | 2 | 92 | 17 | methanol | 2240, 1605 | 2.3(s, 3H); 3.3(t, 2H); 5.05 (t, 2H); 5.15(s, 2H); 7.1-7.5 (m, 6H); 8(d, 2H) |
| 41 | (CH₃O-4 φ-CH₂O)-4 φ- | 2 | 118 | 10 | CH₂Cl₂/ petroleum ether | 2250, 1605 | 3.3(t, 2H); 3.75(s, 3H); 5 (t, 2H); 5.1(s, 2H); 6.8-7.5 (m, 6H); 8(d, 2H) |
| 44 | (CH₃O-3 φ-CH₂O)-4 φ- | 2 | 109 | 34 | methanol | 2240, 1605 | 3.75(s, 3H); 3.3(t, 2H); 5 (t, 2H); 5.15(s, 2H); 6.85-7.5 (m, 6H); 8.05(d, 2H) |
| 46 | (F-4 φ-CH₂O)-4 φ- | 1 | 144 | 60 | methanol | 1615 | 5.15(s, 2H); 6.25(s, 2H); 7-7.65(m, 6H); 8(d, 2H) |
| 47 | (F-4 φ-CH₂O)-4 φ- | 2 | 142 | 45 | methanol | 2250, 1605 | 3.3(t, 2H); 5.05(t, 2H); 5.2 (s, 2H); 7.1-7.65(m, 6H); 8.05(d, 2H) |
| 49 | (NO₂-4 φ-CH₂O)-4 φ- | 2 | 171 | 36 | methanol | 2240, 1610 | 3.3(t, 2H); 5.3(s, 2H); 5 (t, 2H); 5.3(s, 2H); 7.2-7.7 7.8-8.2(4d, 8H) |
| 62 | (I-2 φ-CH₂O)-4 φ- | 2 | 126 | 32 | methanol | 2240 | 3.3(t, 2H); 5(t, 2H); 5.1 (s, 2H); 7.1-8.15(m, 8H) |

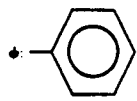

TABLE IV (Ic)

$$Ar_2 \underset{N=N}{\overset{N-N-(CH_2)_m-OH}{\diagdown\diagup}}$$

| Code No. | Ar₂ | m | Melting point (°C.) | Yield (%) | Recrystal. solvent | IR ν cm⁻¹ OH (KBr) | H¹ NMR δ p.p.m. (DMSOd₆) |
|---|---|---|---|---|---|---|---|
| 17 | (φ-CH₂O)-4- φ- | 2 | 113 | 63 | Me OH | 3540 | 3.9(9, 2H), 4.7(t, 2H), 5.5-5.4 (m, 1+2H), 7.1-8.1(m, 9H) |
| 18 | (Cl-2 φ-CH₂O)-4 φ- | 2 | 118 | 41 | Me OH | 3330 | 3.95(q, 2H), 4.75(t, 2H), 5.1(t, 1H), 5.25(s, 2H), 7.2-8.2(m, 8H) |
| 19 | (Cl-3 φ-CH₂O)-4 φ- | 2 | 109 | 36 | Me OH | 3330 | 4(q, 2H), 4.8(t, 2H), 5.1(t, 1H), 5.25(s, 2H), 7.1-8.2(m, 8H) |
| 20 | (Cl-4 φ-CH₂O)-4 φ- | 2 | 132 | 49 | Me OH | 3460 | 4(q, 2H), 4.75(t, 2H), 5.1(t, 1H), 5.2(s, 2H), 7.1-8.2(m, 8H) |
| 21 | (di Cl-2.4 φ-CH₂O)-4 φ- | 2 | 135 | 58 | Me OH | 3380 | 4(q, 2H), 4.75(t, 2H), 5.1(t, 1H), 5.25(s, 2H), 7.15-8.25(m, 7H) |
| 22 | (di Cl-2.6 φ-CH₂O)-4 φ- | 2 | 171 | 56 | Me OH | 3320 | 4(q, 2H), 4.75(t, 2H), 5.1(t, 1H), 5.3(s, 2H), 7.2-8.2(m, 7H) |
| 23 | (di Cl-3.4 φ-CH₂O)-4 φ- | 2 | 126 | 21 | Me OH | 3280 | 4(q, 2H), 4.75(t, 2H), 5.1(t, 1H), 5.2(s, 2H), 7.1-8.2(m, 7H) |
| 24 | φ-4 φ- | 2 | 148 | 52 | Ac OEt | 3460 | 3.95(q, 2H), 4.75(t, 2H), 5.05(t, 1H), 7.2-8.1(m, 9H) |
| 25 | φ-4 φ- | 3 | 102 | 45 | Me OH | 3300 | 1.8-2.1(m, 2H), 3.8(q, 2H), 4.6-4.8 (m, 1+2H), 7.3-8.2(m, 9H) |
| 26 | φ-4 φ- | 4 | 105 | 48 | Me OH | 3300 | 1.3-1.6(m, 2H), 1.7-2.1(m, 2H), 3.45 (q, 2H), 4.5(t, 1H), 4.75(t, 2H), 7.4-8.3(m, 9H) |
| 27 | φ-4 φ- | 6 | 102 | 40 | Me OH | 3280 | 1.15-1.5(m, 6H), 1.8-2.1(m, 2H), 3.35(q, 2H), 4.25(t, 1H), 4.65 |

TABLE IV-continued $$\text{Ar}_2\underset{N\underset{\text{N}}{\underset{\|}{=}}N}{\overset{N-N-(CH_2)_m-OH}{\diagdown\diagup}}$$ (Ic)

| Code No. | Ar₂ | m | Melting point (°C.) | Yield (%) | Recrystal. solvent | IR ν cm⁻¹ OH (KBr) | H¹ NMR δ p.p.m. (DMSOd₆) |
|---|---|---|---|---|---|---|---|
| 28 | (4-pyridyl)- | 2 | 123 | 63 | Me OH | 3190 | (t, 2H), 7.2–8.1(m, 9H) 3.95(q, 2H), 4.8(t, 2H), 5.1(t, 1H), 8.05 et 8.8(2d, 4H) |
| 33 | (CH₃-4 φ-CH₂O)-4 φ- | 2 | 125 | 60 | methanol | 3460, 1615 | 2.6(s, 3H); 3.9(q, 2H); 4.75 (t, 2H); 5.05(t, 1H); 5.15 (s, 2H); 7.1–7.5(m, 6H); 8(d, 2H) |
| 36 | (CH₃-3 φ-CH₂O)-4 φ- | 2 | 100 | 17 | methanol | 3460, 1610 | 2.3(s, 3H); 3.95(q, 2H); 4.75 (t, 2H); 5.05(t, 1H); 5.15 (s, 2H); 6.8–7.5(m, 6H); 8 (d, 2H) |
| 39 | (CH₃-2 φ-CH₂O)-4 φ- | 2 | 94.5 | 24 | methanol | 3300, 1610 | 2.3(s, 3H); 4.7(t, 2H); 3.95 (q, 2H); 5.05(t, 1H); 5.1 (s, 2H); 7.05–7.5(m, 6H); 8(d, 2H) |
| 42 | (CH₃O-4 φ-CH₂O)-4 φ- | 2 | 131 | 52 | methanol | 3480, 1605 | 3.75(s, 3H); 3.95(q, 2H); 4.7 (t, 2H); 5.05(t, 1H); 5.1 (s, 2H); 6.8–7(m, 6H); 7.95 (d, 2H) |
| 45 | (CH₃O-3 φ-CH₂O)-4 φ- | 2 | 105 | 21 | methanol | 3330, 1605 | 3.75(s, 3H); 3.95(q, 2H); 4.75(t, 3H); 5.1(t, 1H); 5.15(s, 2H); 6.8–7.4(m, 6H) 8.05(d, 2H) |
| 48 | (F-4 φ-CH₂O)-4 φ- | 2 | 122 | 52 | methanol | 3490, 1605 | 3.95(q, 2H); 4.7(t, 2H); 5.05 (t, 1H); 5.15(s, 2H); 7.1–7.7 (m, 6H); 8.05(d, 2H) |
| 63 | (I-2 φ-CH₂O)-4 φ- | 2 | 133 | 23 | methanol | 3480 | 3.95(q, 2H); 4.7(t, 2H); 5.05 (t, 1H); 5.1(s, 2H); 7.2–8.05 (m, 8H) |

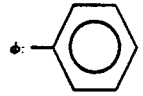

φ:

TABLE V $$\text{Ar}\underset{N\underset{\underset{(CH_2)_p-Z}{\|}}{\underset{\|}{=}}N}{\overset{N-N}{\diagdown\diagup}}$$ (Ib) or (Id)

| Code No. | Ar | p | Z | Melting point (°C.) | Yield (%) | Recrystal. solvent | IR ν cm⁻¹ OH (KBr) | H¹ NMR δ p.p.m. (DMSOd₆) |
|---|---|---|---|---|---|---|---|---|
| 50 | (CH₃-4 φ-CH₂O)-4 φ- | 1 | CN | 166 | 3 | AcOC₂H₅/ petroleum ether | 1605 | 2.3(s, 3H); 5.2(s, 2H); 5.95 (s, 2H); 7.15–7.5(m, 6H); 7.8(d, 2H) |
| 51 | (CH₃O-4 φ-CH₂O)-4 φ- | 2 | OH | 146 | 25 | AcOC₂H₅/ petroleum ether | 3300 1605 | |
| 52 | (F-4 φ-CH₂O)-4 φ- | 1 | CN | 137 | 6 | AcOC₂H₅/ petroleum ether | 1605 | 5.2(s, 2H); 5.95(s, 2H); 7.3–7.8 (2d, 4H); 7.1–7.7(m, 4H) |
| 53 | (F-4 φ-CH₂O)-4 φ- | 2 | OH | 100 | 17 | AcOC₂H₅/ petroleum ether | 3450, 1605 | 3.85(q, 2H); 4.45(t, 2H); 5.1(t, 1H); 5.2(s, 2H); 7.1–7.65 (m, 6H); 7.8(d, 2H) |
| 58 | (I-2 φ-CH₂O)-4 φ- | 2 | OH | 84 | 8 | AcOC₂H₅/ petroleum ether | 3400, 1605 | |
| 59 | (φ-CH₂O)-4 φ- | 1 | CN | 151 | 1.3 | AcOC₂H₅/ petroleum ether | 1605 | |
| 60 | (CH₃-2 φ-CH₂O)-4 φ- | 2 | CN | 101 | 8.1 | AcOC₂H₅/ petroleum ether | 2236, 1605 | |
| 61 | (CH₃-3 φ-CH₂O)-4 φ- | 2 | CN | 103 | 9.4 | AcOC₂H₅/ petroleum | 2245, 1600 | 2.35(s, 3H); 3.2(t, 2H); 4.75 (t, 2H); 5.2(s, 2H); 7.1–7.4 |

TABLE V-continued

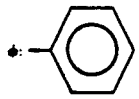

(Ib) or (Id)

| Code No. | Ar | p | Z | Melting point (°C.) | Yield (%) | Recrystal. solvent | IR ν cm⁻¹ OH (KBr) | H¹ NMR δ p.p.m. (DMSOd₆) |
|---|---|---|---|---|---|---|---|---|
| | | | | | | ether | | (m, 6H); 7.75(d, 2H) |

φ: (phenyl)

TABLE VI (Ia), (Ic) or (If)

| Code No. | A | Melting point (°C.) | Yield (%) | Recrystal. solvent | IR ν cm⁻¹ OH (KBr) | H¹ NMR δ p.p.m. (DMSOd₆) |
|---|---|---|---|---|---|---|
| 30 | CH₂OCH₃ | 90 | 20 | methanol | 1610 | 3.4(s, 3H); 5.2(s, 2H); 7.1-7.6(m, 7H); 8.05(d, 2H) |
| 64 | (CH₂)₂—N(CH₃)(CH₃) | 67 | 40 | ether/ petroleum ether | 1610 | 2.15(s, 6H); 2.85(t, 2H); 4.75(t, 2H); 5.15(s, 2H); 7.15 et 8(2d, 4H); 7.3-7.55; (m, 5H) |
| 65 | (CH₂)₂—Br | 110 | 70 | AcOEt/ petroleum ether | 1610 | 4.1(t, 2H); 5.15(s+t, 2+2H) 7.2 et 8.05(2d, 4H); 7.3-7.6 (m 5H) |
| 66 | (CH₂)₂—NH—C(=O)—CH₃ | 142 | 30 | benzene | 3300, 1650 1610 | 1.75(s, 3H); 3.65(t, 2H); 4.75 (t, 2H); 5.15(s, 2H); 7.15 et 7.95(2d, 4H); 7.2-7.5(m, 5H+1H) |
| 67 | (CH₂)₂—N(phthalimide) | 144 | 71 | toluene/ cyclo- hexane | 1770, 1705, 1615 | 4.1(t, 2H); 5(t, 2H); 5.15 (s, 2H); 7.2(d, 2H); 7.3-7.6 (n, 5H); 7.85-8.1(m, 6H) |
| 68 | (CH₂)₂—NH₂ | 108 | 76 | cyclo- hexane/ benzene | 3375, 3300 1615 | 2.2(s, 2H); 3.15(t, 2H); 4.7 (t, 2H); 5.2(s, 2H); 7.25 et 8.1 (2d, 4H); 7.35-7.65(m, 5H) |

EXAMPLE 6

5-(4-benzyloxy phenyl) 3-(2-cyano ethyl) 3H-1,3,4-oxadiazole 2-one [(Ik); code number: 54]

1st step: 1-(4-benzyloxy benzoyl) 2-(2-cyano ethyl) hydrazine (V)

To a solution of 100 mmoles of (4-benzyloxy benzoyl) hydrazine in 200 ml of 1-propanol, 100 mmoles of acrylonitrile are added and the mixture is heated for 24 hours at reflux. Then 50 mmoles of acrylonitrile are added and the heating is continued at reflux for 24 hours. After cooling, the product is filtered and crystallized in a water-ethanol mixture and 26 g (yield: 88%) of the expected product were obtained.

melting point=136° C.
IR (KBr)ν cm⁻¹: 3290, 3220, 2240, 1670.
NMR (DMSO d₆) δ ppm: 3 (t, 2H); 4 (t, 2H); 5.2 (s, 2H); 7-8 (m, 9H).

EXAMPLE 7

5-(4-benzyloxy phenyl) 3-(2-cyano ethyl) 3H-1,3,4-oxadiazole 2-thione [(Il); code number: 55]

To a solution of 10 mmoles of the compound obtained in the first step of example 6 in 100 ml of anhydrous chloroform, 10 mmoles of thiophosgene are added. The mixture obtained is heated for 1 hour at reflux and after concentration and chromatography on a silica column (eluant: CH₂Cl₂) the expected product is obtained with a yield of 85% (recrystallization solvent: ethanol).
melting point = 117° C.
IR (KBr)$\nu$ cm$^{-1}$: 2250, 1610.
NMR (DMSO d$_6$) δ ppm: 3.15 (t, 2H); 4.4 (t, 2H); 5.25 (t, 2H); 7.2–8.15 (m, 9H).

EXAMPLE 8

5-(4-benzyloxy phenyl) 3-(2-cyano ethyl) 3H-1,3,4-thiadiazole 2-one [(Im); code number: 56]

1st step: 1-(4-benzyloxy thiobenzoyl) 2-(2-cyano ethyl) hydrazine (V)

A solution of 25 ml of carbon sulfide in 50 ml of anhydrous THF is added drop by drop to a cooled solution of 4-benzyloxy phenyl magnesium bromide (prepared from 200 mmoles of 4-benzyloxy bromobenzene and 6 g of magnesium in 150 ml of anhydrous THF). The mixture is agitated for 12 hours at room temperature. After addition of 150 g of crushed ice, 25 g of monochloracetic acid and 38 g of sodium carbonate in 250 ml of water, the mixture is left under agitation for 1 week at 25° C. The white precipitate formed is separated by filtration. The aqueous phase is acidified with sulfuric acid and extracted with ether. The organic phase is dried on sodium sulfate and concentrated. Dithio(4-benzyloxy benzoyl) oxyacetic acid is obtained after recrystallization in a benzene/cyclohexane mixture.
yield: 52%.
IR ($\nu$ cm$^{-1}$): 2900, 1680.

This acid (50 mmoles) is dissolved in a 4% NaOH solution (100 ml) and 50 ml of ethanol. Then 75 mmoles of (2-cyano ethyl) hydrazine in solution in 20 ml of ethanol is added. The mixture is heated for 15 minutes at 60°–80° C., cooled to 0° C. and acidified with HCl 6N. By filtration and purification in a hydroalcohol solution, the expected product is obtained with a yield of 38%.
melting point = 135° C.
IR (KBr)$\nu$ cm$^{-1}$: 3260, 3205, 3140, 2250.
NMR (DMSO d$_6$); 6.85 (s, 1H); 7.05–7.75 (2d, 4H); 7.25–7.55 (m, 6H); 12 (s, 1H).

2nd step: 5-(4-benzyloxy phenyl) 3-(2-cyano ethyl) 3H-1,3,4-thiadiazole 2-one (Im)

To a solution of 5 mmoles of the compound obtained in the preceding step in 30 ml of anhydrous dioxane, are added drop by drop at 0° C., 7.5 ml of a 10% phosgene toluene solution. After 30 minutes, the mixture is concentrated and, after recrystallization in 1-butanol, the expected compound is obtained with a yield of 59%.
melting point = 140° C.
IR (KBr)$\nu$ cm$^{-1}$: 2250, 1650, 1600.
NMR (DMSO d$_6$) δ ppm: 3 (t, 2H); 4.15 (t, 2H); 5.15 (s, 2H); 7.15 and 7.65 (2d, 4H); 7.25–7.55 (m, 5H).

EXAMPLE 9

5-(4-benzyloxy phenyl) 3-(2-cyano ethyl) 3H-1,3,4-thiadiazole 2-thione [(In); code number: 57]

To a solution of 55 mmoles of the compound obtained in the first step of example 8 in 30 ml of anhydrous dioxane, 6 mmoles of thiophosgene are added drop by drop with agitation at about 0° C. After 30 minutes, the solvent is evaporated and the remaining product is crystallized in an ethyl acetate/petroleum ether mixture; the expected product is obtained with a yield of 51%.
melting point = 138° C.
IR (KBr)$\nu$ cm$^{-1}$: 2240, 1605.
NMR (DMSO d$_6$) δ ppm: 3.15 (t, 2H); 4.55 (t, 2H); 5.2 (s, 2H); 7.2 and 7.75 (2d, 4H); 7.3–7.55 (m, 5H).

The derivatives (I), their pharmaceutically acceptable salts, as well as 5-phenyl 2-tetrazole butyronitrile and 5-phenyl 2-tetrazole valeronitrile have been tested on laboratory animals and have shown a pharacological activity and particularly an activity of selective inhibitiopn of the monoamine oxidase of type B (MAO-B).

The monoamine oxidase inhibiting activity of these compounds has been revealed by measurements in vitro of the MAO. The quantitative determination of the MAO, activity was made up by using, as enzyme source, a mitochrondrial suspension of the brain of a rat. The standard determination consists in preincubating the enzyme for 20 minutes in the absence then in the presence of the inhibitors. The activities are determined by using respectively serotonine (5-HT) and phenylethylamine (PEA) as substrates of the MAO-A and of MAO-B, the reaction times being 40 minutes with 5-HT and 10 minutes with PEA. The operating method used is that of the protocol of P. C. Baker, Dev. Biol. 14, 267 (1966).

The results expressed in terms of CI$_{50}$ (50% inhibiting concentration) obtained with a certain number of derivatives (I) are shown in tables VII and VIII hereafter.

TABLE VII

| In vitro inhibition of monoamine oxidase | | |
|---|---|---|
| Compound Code No. | IC$_{50}$ (MAO-A) μM | IC$_{50}$ (MAO-B) μM |
| 1 | 150 | 2.2 · 10$^{-3}$ |
| 7 | 86 | 2.3 10$^{-3}$ |
| 13 | 7.8 | 840 · 10$^{-3}$ |
| 14 | 9.6 | 1.2 |
| 16 | 46 | 5.4 |
| 18 | 88 | 5.5 · 10$^{-3}$ |
| 20 | 60 | 8 · 10$^{-3}$ |
| 23 | 140 | 24 · 10$^{-3}$ |
| 27 | 80 | 16.4 |
| 54 | nd | 6.4 · 10$^{-3}$ |
| 55 | nd | 9.3 · 10$^{-3}$ |
| 56 | nd | 1.6 · 10$^{-2}$ |
| 57 | nd | 6.2 · 10$^{-2}$ |
| 30 | nd | 1.6 |
| 42 | nd | 4.7 |
| 50 | nd | 1.5 · 10$^{-2}$ |
| 51 | nd | 0.89 |
| 32 | nd | 0.57 | nd: not determined; too low inhibition

TABLE VIII

| In vitro inhibition of monoamine oxidase | | |
|---|---|---|
| Code No. | IC$_{50}$ (MAO-B) μM | % of inhibition of MAO-A at a concentration of 10$^{-6}$M |
| 29 | 0.1 | 3 |
| 31 | 1.6 | — |
| 33 | 8 | 0 |
| 35 | 0.2 | 5 |
| 36 | 0.3 | 2 |
| 37 | 0.16 | 10 |
| 38 | 0.11 | 6 |
| 39 | 0.29 | 3 |
| 41 | 3.4 | 9 |
| 44 | 0.4 | 0 |
| 45 | 0.8 | 7 |
| 46 | 0.17 | 6 |
| 47 | 0.21 | 2 |
| 48 | 0.27 | 2 |
| 50 | 0.015 | 12 |
| 51 | 0.9 | — |
| 52 | 0.024 | 15 |
| 53 | 0.36 | 3 |
| 58 | 3.6 | 3 |
| 59 | 0.067 | 4 |
| 60 | 0.48 | 17 |

TABLE VIII-continued

| | In vitro inhibition of monoamine oxidase | |
|---|---|---|
| Code No. | IC$_{50}$ (MAO-B) μM | % of inhibition of MAO-A at a concentration of $10^{-6}$M |
| 61 | 0.27 | 1 |
| 64 | 0.28 | 15 |
| 65 | 0.09 | 4 |
| 66 | 1.5 | 3.7 |
| 68 | 0.07 | 6 |

In so far as the toxicity of the derivatives of the invention is concerned, it will be noted by way of example that after oral administration to mice of the compounds of code numbers 1, 7, 17 or 19 up to a dose of 1500 mg/kg, no toxicity was observed for 24 hours.

The derivatives (I), their pharmaceutically acceptable salts, as well as 5-phenyl 2-tetrazole butyronitrile and 5-phenyl 2-tetrazole valeronitrile may therefore be used for preparing MAO-B inhibiting medicaments, these medicaments finding their use in therapeutics, particularly for the treatment of neurological troubles related to pathologic ageing, mnesic troubles, humours, schizophrenia, psychiastenia or psychic slowing down due to ageing, certain forms of depression and Parkinson's disease.

These medicaments may be administered to man or any warm blooded animal, in different pharmaceutical forms well known in the technique considered, and particularly in the form of compositions formulated for oral, parenteral or rectal administration.

For oral administration, said compositions may be in the form of tablets, pills or capsules, prepared by the usual techniques using known carriers and excipients such as binding agents, charges, lubricants and disintegration agents; they may also be in the form of solutions, syrups or suspensions.

For parenteral administration, the compositions of the invention may be in the form of injectable solutions, suspensions or emulsions comprising a liquid, oily or aqueous, vehicle parenterally acceptable.

For rectal administration, the compositions may be in the form of suppositories comprising the usual bases for suppositories.

The therapeutically active dose of the active substances, namely derivatives (I), their pharmaceutically acceptable salts, as well as 5-phenyl 2-tetrazole butyronitrile and 5-phenyl 2-tetrazole valeronitrile, depends more particularly on the way of administration, on the body weight of the patient and on the therapeutic power of the active substances used. Generally, orally, the amounts administered may reach 600 mg of active substance per day (taken in one or more doses); parenterally, they may reach 100 mg of active substance per day (taken in one or more daily injections); and rectally, they may reach 300 mg of active substance per day (in one or more suppositories).

We claim:

1. Derivatives of formula:

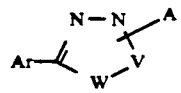

in which the chain

represents 1) either the chain of structure:

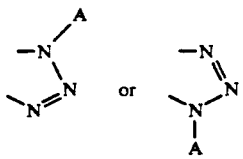

where A is:

a) a vinyl group or a $(CH_2)_n$—$Z_1$ group in which $Z_1$ represents a CN, methoxy or ethoxy group and n is an integer from 1 to 6, in which case Ar takes on the value Ar$_1$ which represents:

a phenyl nucleus substituted by benzyloxy group of formula:

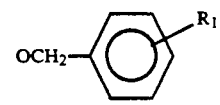

where R$_1$ represents a hydrogen atom, one or two halogen atoms or a CN, NO$_2$, NH$_2$, CF$_3$, C$_1$-C$_4$ alkyl, C$_1$-C$_4$ alkoxy or C$_2$-C$_4$ acylamino group; or b) a group of formula $(CH_2)_m$—$Z_2$ in which $Z_2$ represents an OH group, a halogen atom, an NH$_2$, an NH$_2$ group substituted by one or two C$_1$-C$_4$ alkyl groups, a C$_2$-C$_4$ acylamino group or a phthalimido group and m is an integer from 2 to 6, in which case Ar takes on the value Ar$_2$ which represents:

a phenyl nucleus substituted by a benzyloxy group of formula

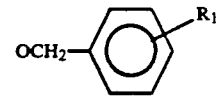

where R$_1$ has the same meaning as above; as well as the pharmaceutically acceptable acid addition salts of these derivatives (I) having a salifiable group, with the exclusion of 5-phenyl 2-tetrazole butyronitrile and 5-phenyl 2-tetrazole valeronitrile.

2. Derivatives according to claim 1, of structure:

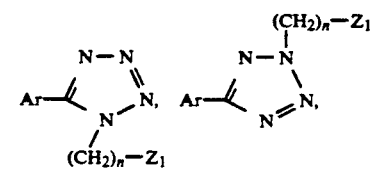

-continued

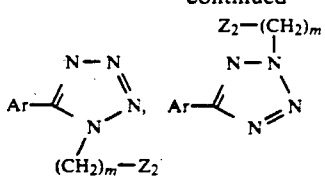

where $Z_1 = CN$, $n = 1$ or 2, $Z_2 = OH$, $m =$ integer from 2 to 6 and Ar represents a phenyl nucleus para substituted by a benzyloxy group whose phenyl nucleus is possibly substituted by one or two halogen atoms or a $C_1$-$C_4$ alkyl or $C_1$-$C_4$ alkoxy group.

3. Compounds of formula:

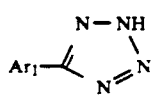 (IIIa)

where $Ar_1$ represents:
a phenyl nucleus substituted by benzyloxy group of formula:

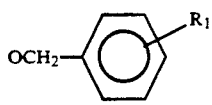

where $R_1$ represents a hydrogen atom, one or two halogen atoms or a CN, $NO_2$, $NH_2$, $CF_3$, $C_1$-$C_4$ alkyl, $C_1$-$C_4$ alkoxy or $C_2$-$C_4$ acylamino.

4. A compound of the formula

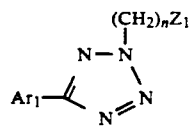

in which
$Z_1$ is CN or OH
n is 1 or 2, and
$Ar_1$ is

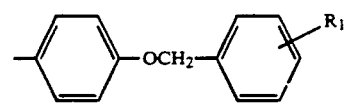

wherein $R_1$ is H, one or two halogens, or CN, $NO_2$, $NH_2$, $CF_3$, $C_1$-$C_4$ alkyl, $C_1$-$C_4$ alkoxy or $C_2$-$C_4$ acylamino.

5. A compound as claimed in claim 4 in which $Z_1$ is CN, n is 2 and $R_1$ is hydrogen.
6. A compound as claimed in claim 4 in which $Z_1$ is OH, n is 2 and $R_1$ is hydrogen.
7. A compound as claimed in claim 4 in which Z is OH, n is 2 and $R_1$ is 2-Cl.
8. A compound as claimed in claim 4 in which $Z_1$ is OH, n is 2 and $R_1$ is 3-Cl.
9. A compound as claimed in claim 4 in which $Z_1$ is OH, n is 2 and $R_1$ is 4-Cl.
10. A compound as claimed in claim 4 in which $Z_1$ is OH, n is 2 and $R_1$ is 2,4-diCl.
11. A compound as claimed in claim 4 in which $Z_1$ is OH, n is 2 and $R_1$ is 2,6-diCl.
12. A compound as claimed in claim 4 in which $Z_1$ is OH, n is 2 and $R_1$ is 3,4-diCl.
13. A compound of the formula

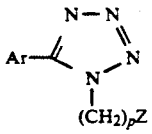

in which
Z is CN or OH
p is 1 or 2, and
Ar is

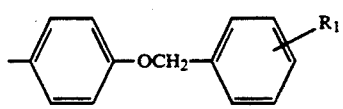

wherein $R_1$ is H, one or two halogens, or CN, $NO_2$, $NH_2$, $CF_3$, $C_1$-$C_4$ alkyl, $C_1$-$C_4$ alkoxy or $C_2$-$C_4$ acylamino.

14. A compound as claimed in claim 13 in which Z is CN, p is 1 and $R_1$ is 4-$CH_3$.
15. A compound as claimed in claim 13 in which Z is OH, p is 2 and $R_1$ is 4-$CH_3$.
16. A compound as claimed in claim 13 in which Z is OH, p is 2 and $R_1$ is 4-F.
17. A compound of the formula

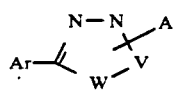

in which

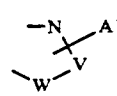

is

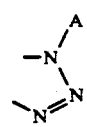

or

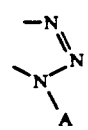

where A is either
(a) vinyl or $(CH_2)_n$—$Z_1$ in which $Z_1$ is CN, methoxy or ethoxy, and n is an integer of from 1 to 6 or
(b) $(CH_2)_m$—$Z_2$, in which $Z_2$ is OH, halogen, $NH_2$, $NH_2$ substituted with one or two $C_1$-$C_4$ alkyls, $C_2$-$C_4$ acylamino or phthalimido, and m is an integer from 2 to 6 with the proviso that when A is (a), Ar is phenyl substituted by

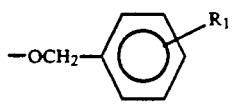

in which $R_1$ is hydrogen, one or two halogens, or CN, $NO_2$, $NH_2$, $CF_3$, $C_1$-$C_4$ alkyl, $C_1$-$C_4$ alkoxy or $C_2$-$C_4$ acylamino, and when A is (b), Ar is phenyl substituted with $C_1$-$C_4$ alkoxy or

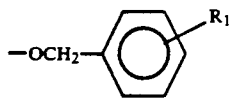

in which $R_1$ has the same meaning as defined above.

18. A pharmaceutical composition comprising a therapeutically effective amount of a compound of formula (I):

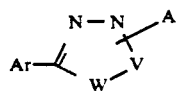     (I)

in which the chain

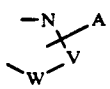

represents either the chain of structure

where A is
a) a vinyl group or a $(CH_2)_n$—$Z_1$ group in which $Z_1$ represents a CN, methoxy or ethoxy group and n is an integer from 1 to 6, in which case Ar takes on the value $Ar_1$ which represents a phenyl nucleus substituted by a benzyloxy group of formula

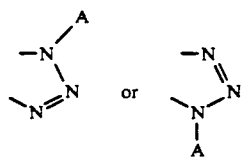

where $R_1$ represents a halogen atom, one or two halogen atoms or a CN, $NO_2$, $NH_2$, $CF_3$, $C_1$-$C_4$ alkyl, $C_1$-$C_4$ alkoxy or $C_2$-$C_4$ acylamino group; or
b) a group of formula $(CH_2)_m$—$Z_2$ in which $Z_2$ represents an OH group, a halogen atom, an $NH_2$ group, an $NH_2$ group substituted by one or two $C_1$-$C_4$ alkyl groups, a $C_2$-$C_4$ acylamino group or a phthalimido group and m is an integer from 2 to 6, in which case Ar takes on the value $Ar_2$ which represents a phenyl nucleus substituted by a benzyloxy group of formula

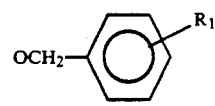

where $R_1$ has the same meaning as above, or a pharmaceutically acceptable salt thereof, with the exclusion of 5-phenyl-2-tetrazole butyronitrile or and 5-phenyl-2-tetrazole valeronitrile, combined with a pharmaceutically acceptable carrier or excipient.

19. A method of treating a patient to inhibit type B monoamine oxidase which comprises administering to the patient a therapeutically effective amount of a compound of formula (I)

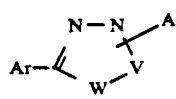     (I)

in which the chain

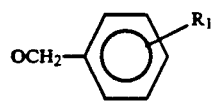

1) either the chain of structure

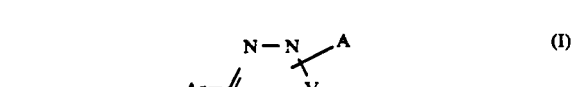

where A is
a) a vinyl group or a $(CH_2)_n$—$Z_1$ group in which $Z_1$ represents a CN, methoxy or ethoxy group and n is an integer from 1 to 6, in which case Ar takes on the value $Ar_1$ which represents a phenyl nucleus;
a phenyl nucleus substituted by one or two halogen atoms or an $NO_2$, methyl, ethyl, methoxy, ethoxy, phenyl or benzyloxy group of formula

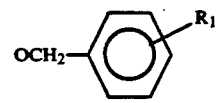

where $R_1$ represents a hydrogen atom, one or two halogen atoms or a CN, $NO_2$, $CF_3$, $C_1$-$C_4$ alkyl, $C_1$-$C_4$ alkoxy or $C_2$-$C_4$ acylamino group; or
b) a group of formula $(CH_2)_m$—$Z_2$ in which $Z_2$ represents an OH group, a halogen atom, an $NH_2$, an $NH_2$ group substituted by one or two $C_1$-$C_4$ alkyl groups, a $C_2$-$C_4$ acylamino group or a phthalimido group and m is an integer from 2 to 6, in which case Ar takes on the value $Ar_2$ which represents a phenyl nucleus substituted by a $C_1$–$C_4$ alkoxy group
or a benzyloxy group of formula
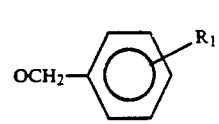
where $R_1$ has the same meaning as above; or a pharmaceutically acceptable salt thereof with exclusion of 5-phenyl 2-tetrazole butyronitrile and 5-phenyl 2-tetrazole valeronitrile.
* * * * *

UNITED STATES PATENT AND TRADEMARK OFFICE
CERTIFICATE OF CORRECTION

PATENT NO. : 5 100 910
DATED : March 31, 1992
INVENTOR(S) : René L. MILCENT et al It is certified that error appears in the above-identified patent and that said Letters Patent is hereby corrected as shown below:

Column 20, line 23; change "benzyloxy" to ---a benzyloxy---.
Column 21, line 23; change "benzyloxy" to ---a benzyloxy---.
Column 21, line 61; change "Z is" to ---Z, is---.
Column 23, line 60; change "halogen" to ---hydrogen---.
Column 24, line 11; delete "or".
Column 24, line 31; after formula insert ---represents---.
Column 26, line 8; change "thereof with" to ---thereof, with the---.

Signed and Sealed this

Third Day of August, 1993

Attest:

MICHAEL K. KIRK

Attesting Officer

Acting Commissioner of Patents and Trademarks